US011065071B2

(12) United States Patent
Kurihara et al.

(10) Patent No.: US 11,065,071 B2
(45) Date of Patent: Jul. 20, 2021

(54) MEDICAL MANIPULATOR SYSTEM AND OPERATING METHOD THEREOF

(71) Applicant: OLYMPUS CORPORATION, Tokyo (JP)

(72) Inventors: Kyohei Kurihara, Tokyo (JP); Mitsuaki Hasegawa, Tokyo (JP); Hiroyuki Hashimoto, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 504 days.

(21) Appl. No.: 16/005,844

(22) Filed: Jun. 12, 2018

(65) Prior Publication Data

US 2018/0289437 A1     Oct. 11, 2018

Related U.S. Application Data

(63) Continuation of application No. PCT/JP2015/084994, filed on Dec. 15, 2015.

(51) Int. Cl.
*G05B 15/00* (2006.01)
*G05B 19/00* (2006.01)
(Continued)

(52) U.S. Cl.
CPC .............. *A61B 34/70* (2016.02); *A61B 34/30* (2016.02); *A61B 34/74* (2016.02); *B25J 9/1643* (2013.01);
(Continued)

(58) Field of Classification Search
CPC ......... A61B 34/30; A61B 34/70; A61B 90/10; A61B 2090/061; A61B 2090/0801;
(Continued)

(56) References Cited

U.S. PATENT DOCUMENTS

2004/0024311 A1* 2/2004 Quaid, III .............. A61B 34/10
600/428
2004/0034282 A1 2/2004 Quaid, III
(Continued)

FOREIGN PATENT DOCUMENTS

JP    2000-300579 A    10/2000
JP    2004-081277 A     3/2004
(Continued)

OTHER PUBLICATIONS

International Search Report dated Mar. 8, 2016 issued in PCT/JP2015/084994.

*Primary Examiner* — Harry Y Oh
(74) *Attorney, Agent, or Firm* — Scully, Scott, Murphy & Presser, P.C.

(57) ABSTRACT

A medical manipulator system including: a placement table on which a patient is placed; at least one manipulator configured to support a treatment tool which is configured to treat the patient, the manipulator configured to adjust a position and an orientation of the treatment tool; a base portion configured to support the manipulator; a sensor configured to detect objects which are present in a predetermined area including the manipulator and the placement table; and a controller including at least one processor, wherein the processor is configured to: calculate degrees of proximity between the objects detected by the sensor and the manipulator, and generate, in case that the calculated degrees of proximity exceed a predetermined threshold, a control signal for preventing interference between the objects and the manipulator.

16 Claims, 6 Drawing Sheets

(51) Int. Cl.
  *A61B 34/00* (2016.01)
  *B25J 9/16* (2006.01)
  *A61B 34/30* (2016.01)
  *A61B 90/00* (2016.01)
  *A61B 90/10* (2016.01)
  *A61B 90/50* (2016.01)

(52) U.S. Cl.
  CPC ............ *B25J 9/1676* (2013.01); *A61B 90/10* (2016.02); *A61B 90/50* (2016.02); *A61B 2090/061* (2016.02); *A61B 2090/0801* (2016.02); *G05B 2219/39083* (2013.01)

(58) Field of Classification Search
  CPC ........ A61B 34/74; A61B 90/50; B25J 9/1676; G05B 2219/39083
  See application file for complete search history.

(56) References Cited

U.S. PATENT DOCUMENTS

| | | |
|---|---|---|
| 2004/0034283 A1 | 2/2004 | Quaid, III |
| 2004/0034302 A1 | 2/2004 | Abovitz et al. |
| 2004/0106916 A1* | 6/2004 | Quaid ..................... A61B 34/76 606/1 |
| 2006/0142657 A1* | 6/2006 | Quaid ................. A61B 17/1764 600/424 |
| 2007/0142751 A1 | 6/2007 | Kang et al. |
| 2009/0000626 A1 | 1/2009 | Quaid et al. |
| 2009/0000627 A1 | 1/2009 | Quaid et al. |
| 2009/0012531 A1 | 1/2009 | Quaid et al. |
| 2009/0012532 A1 | 1/2009 | Quaid et al. |
| 2009/0192524 A1* | 7/2009 | Itkowitz ................. A61B 90/36 606/130 |
| 2009/0326556 A1* | 12/2009 | Diolaiti .............. A61B 1/00009 606/130 |
| 2010/0137882 A1 | 6/2010 | Quaid, III |
| 2011/0245844 A1* | 10/2011 | Jinno ..................... A61B 34/37 606/130 |
| 2012/0059391 A1* | 3/2012 | Diolaiti .................. B25J 9/1689 606/130 |
| 2012/0109150 A1 | 5/2012 | Quaid et al. |
| 2012/0109152 A1 | 5/2012 | Quaid, III |
| 2012/0209069 A1* | 8/2012 | Popovic ................. A61B 5/065 600/109 |
| 2013/0172902 A1 | 7/2013 | Lightcap et al. |
| 2013/0203024 A1* | 8/2013 | Dekar .................... A47G 21/08 434/127 |
| 2013/0211588 A1* | 8/2013 | Diolaiti .................... B25J 13/06 700/249 |
| 2013/0325031 A1* | 12/2013 | Schena .................. A61B 34/30 606/130 |
| 2013/0325032 A1* | 12/2013 | Schena .................. A61B 34/30 606/130 |
| 2015/0320500 A1 | 11/2015 | Lightcap et al. |
| 2016/0228204 A1 | 8/2016 | Quaid et al. |
| 2016/0278870 A1 | 9/2016 | Quaid et al. |
| 2016/0346050 A1 | 12/2016 | Schena et al. |
| 2017/0151021 A1 | 6/2017 | Quaid, III |
| 2018/0021097 A1 | 1/2018 | Quaid et al. |
| 2018/0064492 A1 | 3/2018 | Lightcap et al. |
| 2018/0289445 A1* | 10/2018 | Krinninger ............ A61B 34/25 |

FOREIGN PATENT DOCUMENTS

| | | |
|---|---|---|
| JP | 2004-223128 A | 8/2004 |
| JP | 2005-137770 A | 6/2005 |
| JP | 2007-534351 A | 11/2007 |
| JP | 2015-051287 A | 3/2015 |
| JP | 2015-519146 A | 7/2015 |
| WO | WO 2005/009215 A2 | 2/2005 |
| WO | WO 2010/117685 A2 | 10/2010 |
| WO | WO 2013/181526 A1 | 12/2013 |

* cited by examiner

MEDICAL MANIPULATOR SYSTEM AND OPERATING METHOD THEREOF

This is a continuation of International Application PCT/JP2015/084994, with an international filing date of Dec. 15, 2015, which is hereby incorporated by reference herein in its entirety.

TECHNICAL FIELD

The present invention relates to a medical manipulator system and an operating method thereof.

BACKGROUND ART

There is a known medical manipulator system in which, by providing redundant joints in multi-joint manipulators, interference between manipulators is prevented by allowing the positions of manipulator joints to be changed without moving a treatment tool (for example, see Patent Literature 1).

CITATION LIST

Patent Literature

{PTL 1} U.S. Patent Application Publication No. 2013/325031, Specification

SUMMARY OF INVENTION

An aspect of the present invention is a medical manipulator system including: a placement table on which a patient is placed; at least one manipulator configured to support a treatment tool which is configured to treat the patient, the manipulator configured to adjust a position and an orientation of the treatment tool; a base portion configured to support the manipulator; a sensor configured to detect objects which are present in a predetermined area including the manipulator and the placement table; and a controller including at least one processor, wherein the processor is configured to: calculate degrees of proximity between the objects detected by the sensor and the manipulator, and generate, in case that the calculated degrees of proximity exceed a predetermined threshold, a control signal for preventing interference between the objects and the manipulator.

Another aspect of the present invention is a controller for a medical manipulator system, the medical manipulator system including a placement table, at least one manipulator configured to support a treatment tool, and a sensor configured to detect objects which are present in a predetermined area including the manipulator and the placement table, the controller including: at least one processor, wherein the processor is configured to: calculate degrees of proximity between the objects detected by the sensor and the manipulator, and generate, in case that the calculated degrees of proximity exceed a predetermined threshold, a control signal for preventing interference between the objects and the manipulator.

Another aspect of the present invention is a method of controlling a medical manipulator system, the medical manipulator system including a placement table, at least one manipulator configured to support a treatment tool, and a sensor configured to detect objects which are present in a predetermined area including the manipulator and the placement table, the method comprising: calculating degrees of proximity between the objects detected by the sensor and the manipulator, and generating, in case that the calculated degrees of proximity exceed a predetermined threshold, a control signal for preventing interference between the objects and the manipulator.

DESCRIPTION OF EMBODIMENT

A medical manipulator system 1 according to an embodiment of the present invention and an operating method thereof will be described below with reference to the drawings.

Figure 1:
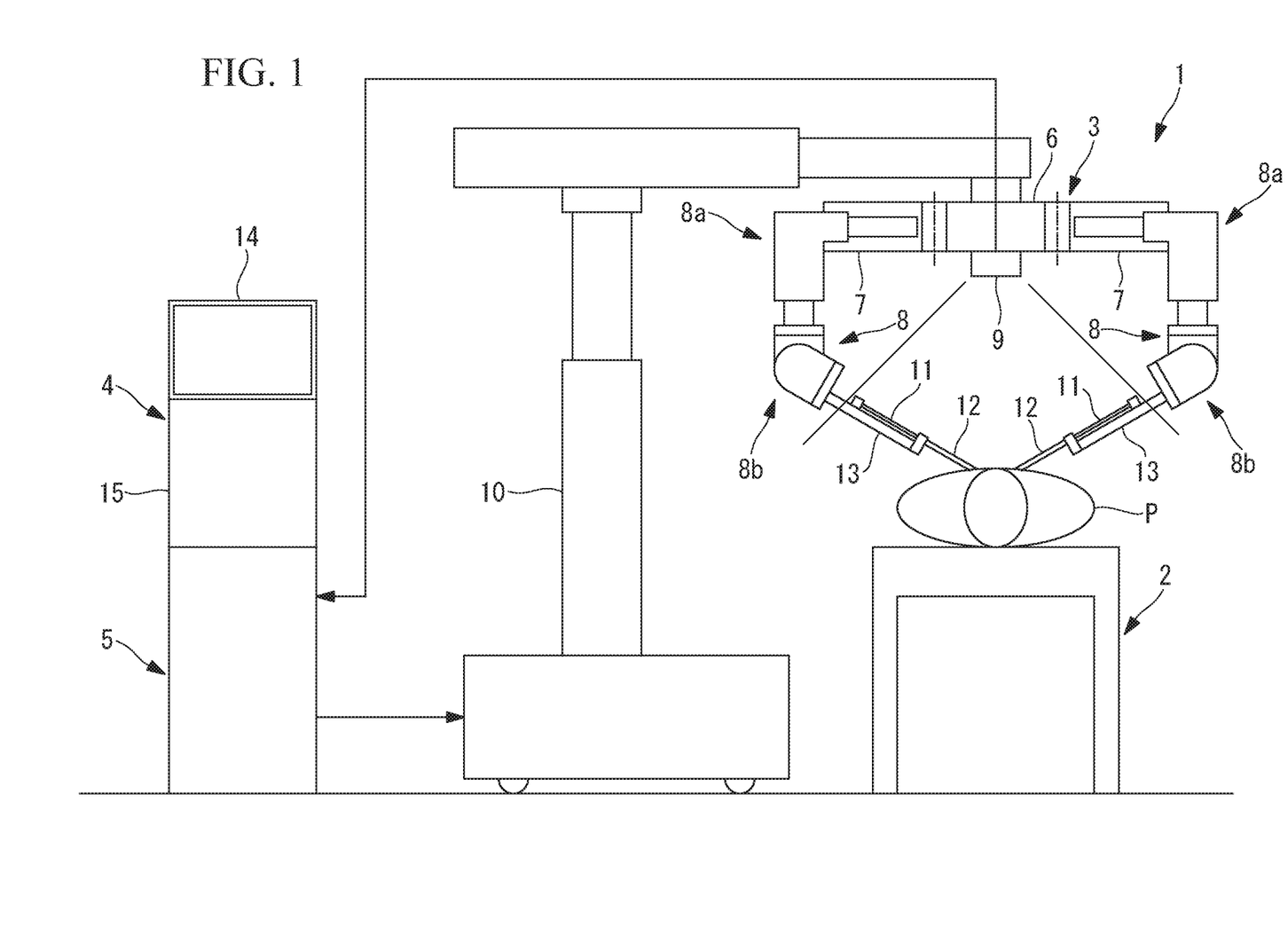
FIG. 1 is an overall configuration diagram showing a medical manipulator system according to an embodiment of the present invention.

As shown in FIG. 1, the medical manipulator system 1 according to this embodiment includes: a bed (placement table) 2 on which a patient P is laid down; a manipulator unit 3 that is disposed beside the bed 2; a manipulating portion 4 that is manipulated by an operator; and a control portion 5.

The manipulator unit 3 includes: a base portion 6 that is disposed above the bed 2 with a spacing therefrom; a plurality of manipulators 8 that include linkages 7 extending radially outward from the base portion 6; a sensor 9 that has a downward-pointing detection area at a center of a bottom surface of the base portion 6; and a base driving portion 10 that supports the base portion 6 so as to be movable in at least one of the horizontal direction and the vertical direction.

The base driving portion 10 is configured so as to allow the position of the base portion 6 with respect to the patient P to be three-dimensionally adjusted. Note that, as the base driving portion 10, a unit having a structure to be secured to the ceiling may be employed, aside from a unit having structure to be erected at a side of the bed 2.

Each of the manipulators 8 is a multi-joint manipulator in which a plurality of linkages are connected by a plurality of joints, and is provided with, at a distal end thereof, an equipment holder 13 that supports a treatment tool 11 and the trocar 12. The manipulators 8 are configured so that it is possible, by moving the plurality of joints, to adjust the positions and orientations of the treatment tools 11 and the trocars 12 that are supported by the equipment holders 13.

Figure 2:
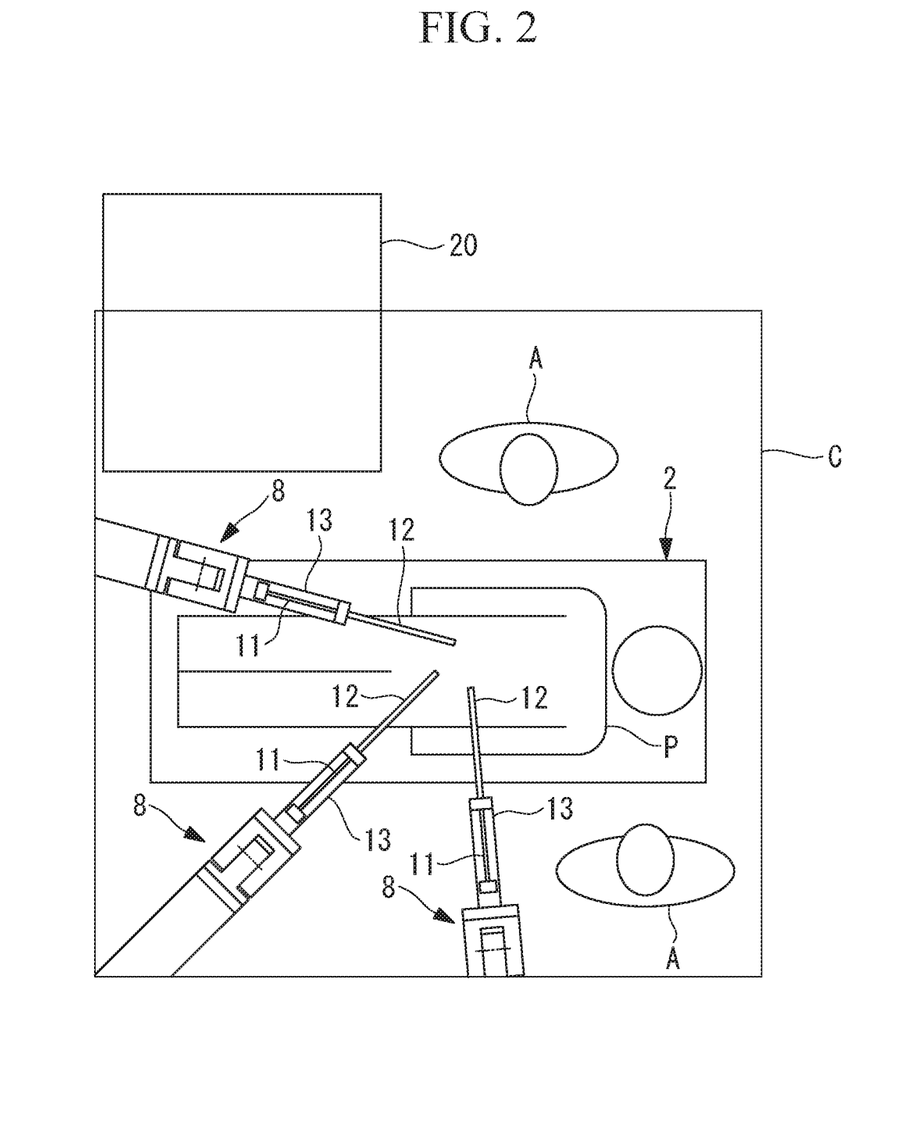
FIG. 2 is a diagram showing an example of an image acquired by a sensor provided in the medical manipulator system in FIG. 1.

The sensor 9 is, for example, a 3D camera. As shown in FIG. 2, the sensor 9 has a viewing-field area (detection area) C that extends so as to include the bed 2 and at least portions of the manipulators 8. The sensor 9 is configured so that it is possible, by recognizing objects (the bed 2, the patient P, an assistant A, the manipulators 8, medical equipment 20, etc.) placed in the viewing-field area C, to acquire information that allows detection of the three-dimensional positions of individual portions of the objects.

Note that, between the base portion 6 and the sensor 9, a movable portion (not shown) for adjusting the position of the sensor 9 may be provided. By allowing the movable portion to be manipulated by using the manipulating portion 4, an operator can appropriately adjust the position of the sensor 9. Alternatively, the position of the sensor 9 may be automatically adjusted by moving the movable portion by means of the control portion 5 on the basis of image information or the like acquired by the sensor 9. Furthermore, the movable portion may be freely attachable to and detachable from the sensor 9.

The manipulating portion 4 includes a manipulation input portion 15 that is manipulated by the operator and a monitor 14 that displays an image of a body interior of the patient P acquired by using an endoscope (not shown) mounted to one of the manipulators 8. The operator manipulates the manipulation input portion 15 while viewing an affected portion and a distal-end portion of the treatment tool 11 attached to one of the manipulators 8 in the image of the body interior of the patient P displayed on the monitor 14. By so doing, the operator can treat the affected portion by moving the manipulators 8 and the treatment tool 11.

Figure 3:
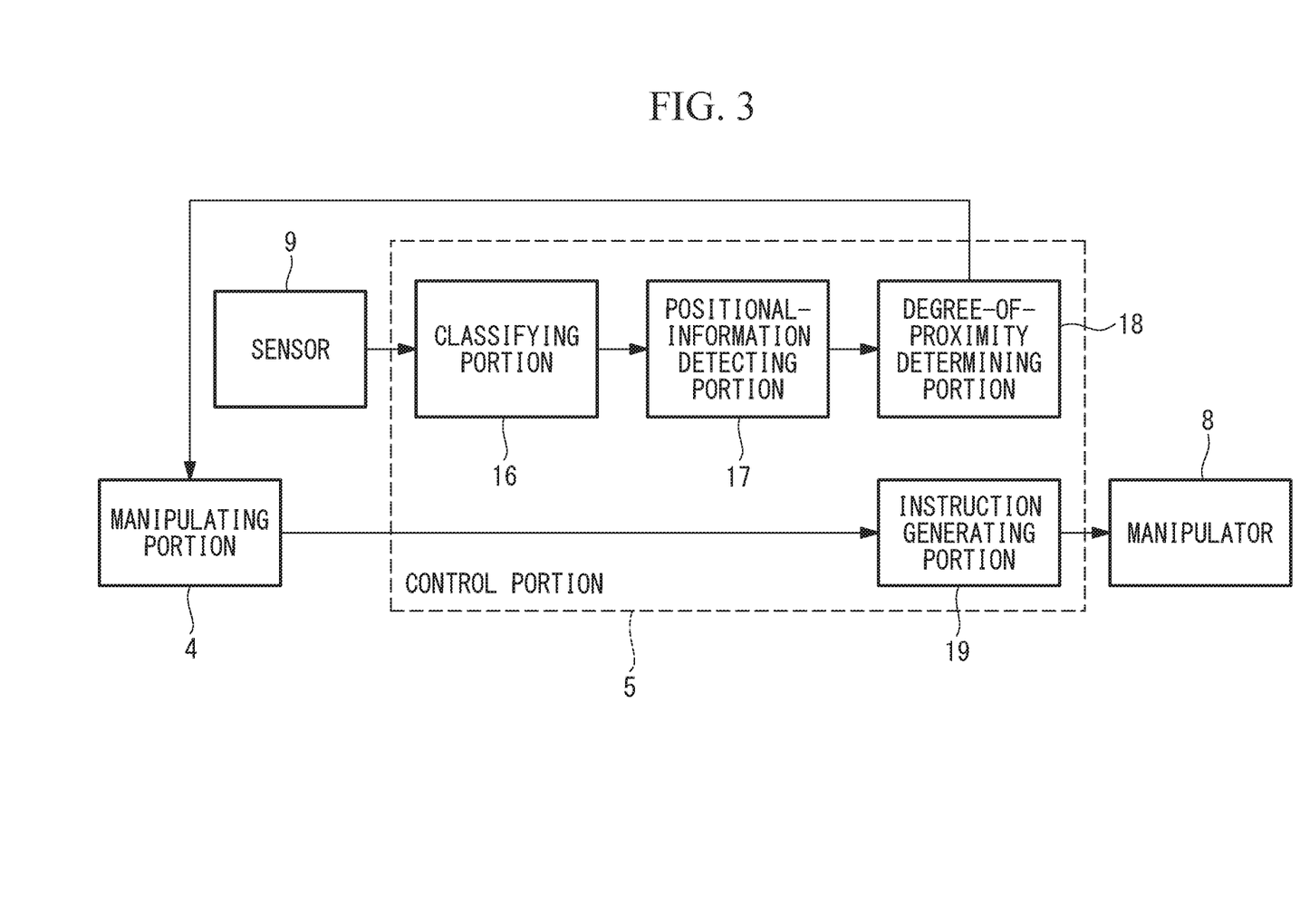
FIG. 3 is a block diagram showing the medical manipulator system in FIG. 1.

As shown in FIG. 3, the control portion 5 includes: a classifying portion 16, a positional-information detecting portion 17, a degree-of-proximity determining portion 18, and an instruction generating portion 19. The classifying portion 16 recognizes and classifies the objects in the viewing-field area on the basis of the image acquired by the sensor 9. The positional-information detecting portion 17 detects positional information of the individual portions of the objects classified by the classifying portion 16. The degree-of-proximity determining portion 18 determines degrees of proximity on the basis of the positional information detected by the positional-information detecting portion 17. The instruction generating portion 19 generates motion instructions for moving the manipulators 8 and the treatment tool 11 on the basis of manipulations input via the manipulation input portion 15.

The control portion 5 ascertains joint angles of the individual manipulators 8. Therefore, the control portion 5 successively calculates and retains the positional information of the individual portions of the manipulators 8 in accordance with the joint angles.

The degree-of-proximity determining portion 18 is configured so as to calculate, on the basis of the detected positional information of the individual portions of various objects and the positional information of the individual portions of the individual manipulators 8 retained by the degree-of-proximity determining portion 18 itself, degrees of proximity (for example, distances) that indicate how close the objects and the manipulators 8 are. Then, in the case in which the calculated degrees of proximity exceed a predetermined threshold, in other words, in the case in which the manipulators 8 and the objects are too close to each other, the degree-of-proximity determining portion 18 transmits a signal indicating this fact to the manipulating portion 4.

When the signal indicating that the manipulators 8 and the objects are too close to each other is transmitted from the control portion 5, the manipulating portion 4 displays this information on the monitor 14, thus calling the attention of the operator. For example, at least part of a screen of the monitor 14 is made to flicker in red or the like, thus making the operator aware of the situation. In other words, the monitor 14 of the manipulating portion 4 is configured so as to serve as a notifying portion.

An operating method of the thus-configured medical manipulator system 1 according to this embodiment will be described below.

In order to treat a patient P by using the medical manipulator system 1 according to this embodiment, by operating the base driving portion 10, the base portion 6 is placed at an appropriate position in the horizontal direction with an appropriate spacing above the bed 2.

Next, the patient P is laid down on the bed 2, and, for example, a plurality of trocars 12 are placed in the abdomen of the patient P by passing therethrough. Then, the distal end of the treatment tool 11 is placed inside the body via one of the trocars 12, and, subsequently, portions of said trocar 12 and treatment tool 11 that are exposed to outside the body are secured to the equipment holder 13 at the distal end of one of the manipulators 8. Similarly, the distal end of the endoscope is placed inside the body via another trocar 12 that has been placed in the abdomen of the patient P by passing therethrough, and, subsequently, portions of said trocar 12 and endoscope that are exposed to outside the body are secured to the equipment holder 13 of the other manipulator 8.

In this state, an image of the body interior of the patient P acquired by the endoscope and an image of the distal-end portion of the treatment tool 11 placed in the viewing-field area of the endoscope are displayed on the monitor 14 of the manipulating portion 4. At this point, the operator starts to operate the manipulating portion 4 and the manipulator unit 3 in an interlinked manner.

Then, when the operator manipulates the manipulation input portion 15, the control portion 5 generates the motion instructions in accordance with the manipulation inputs and causes the manipulators 8 and the treatment tool 11 to be operated, and thus, it is possible to treat an affected portion inside the body of the patient P.

Figure 4:
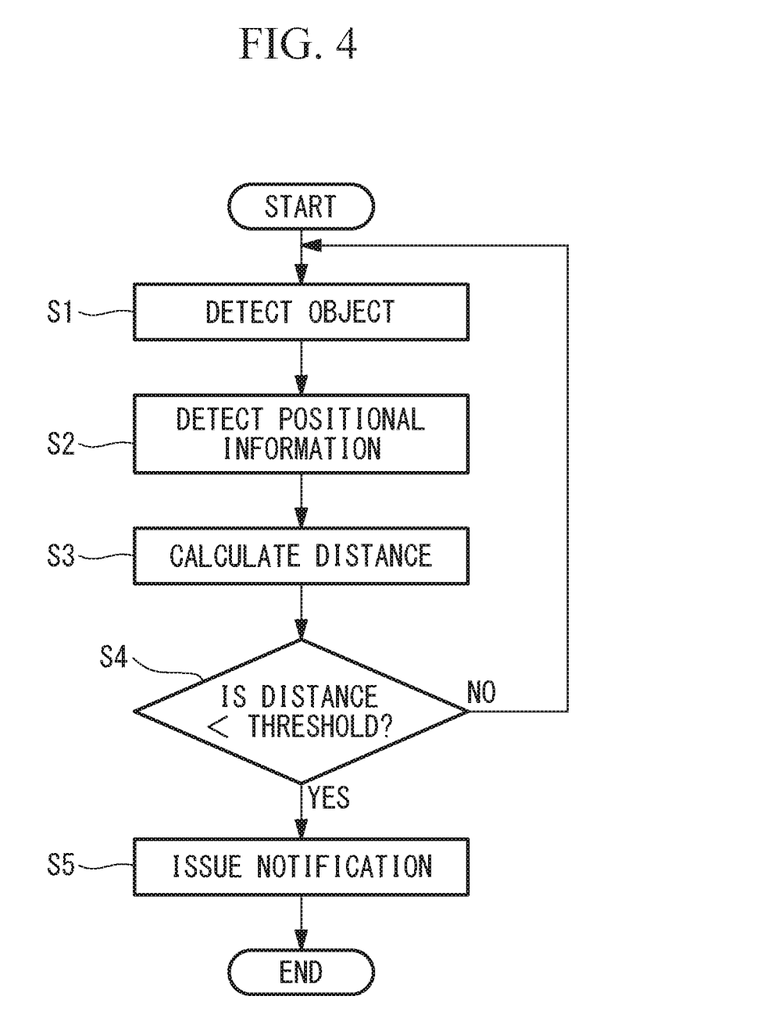
FIG. 4 is a flowchart for explaining an operating method of the medical manipulator system in FIG. 1.

In this case, as shown in FIG. 4, by transmitting the image acquired by the sensor 9 disposed at the center of a bottom surface of the base portion 6 to the control portion 5, in the control portion 5, the objects that are present in the image acquired by the sensor 9, such as the bed 2, the patient P, the assistant A, the manipulators 8, the medical equipment 20, etc., are recognized and classified (step S1), the positional information of the individual portions of the objects is detected (step S2), and, on the basis of the detected positional information, the distances between the manipulators 8 being manipulated and other objects are calculated (step S3). Among the distances between the manipulators 8 being manipulated and other objects, whether or not the smallest distance is less than the predetermined threshold is determined (step S4), and, if said distance is less than the threshold, the control portion 5 transmits the signal indicating this fact to the manipulating portion 4.

In the case in which the signal indicating the fact that the manipulators 8 being manipulated are getting abnormally close to other objects is transmitted from the control portion 5, the manipulating portion 4 displays this information on the monitor 14 (step S5).

By doing so, it is possible to call the attention of the operator, who is performing manipulations while viewing only the monitor 14, to the fact the manipulators 8 being manipulated are, at any of the positions thereof, getting close to other objects.

When the operator who has recognized the fact that the manipulators 8 being manipulated are, at any of the positions thereof, getting close to other objects stops performing manipulation inputs via the manipulation input portion 15, it is possible to prevent the manipulators 8 being manipulated from getting any closer to other objects. In other words, with the medical manipulator system 1 according to this embodiment, there is an advantage in that it is possible to avoid interference between the manipulators 8 and other objects.

Figure 5:
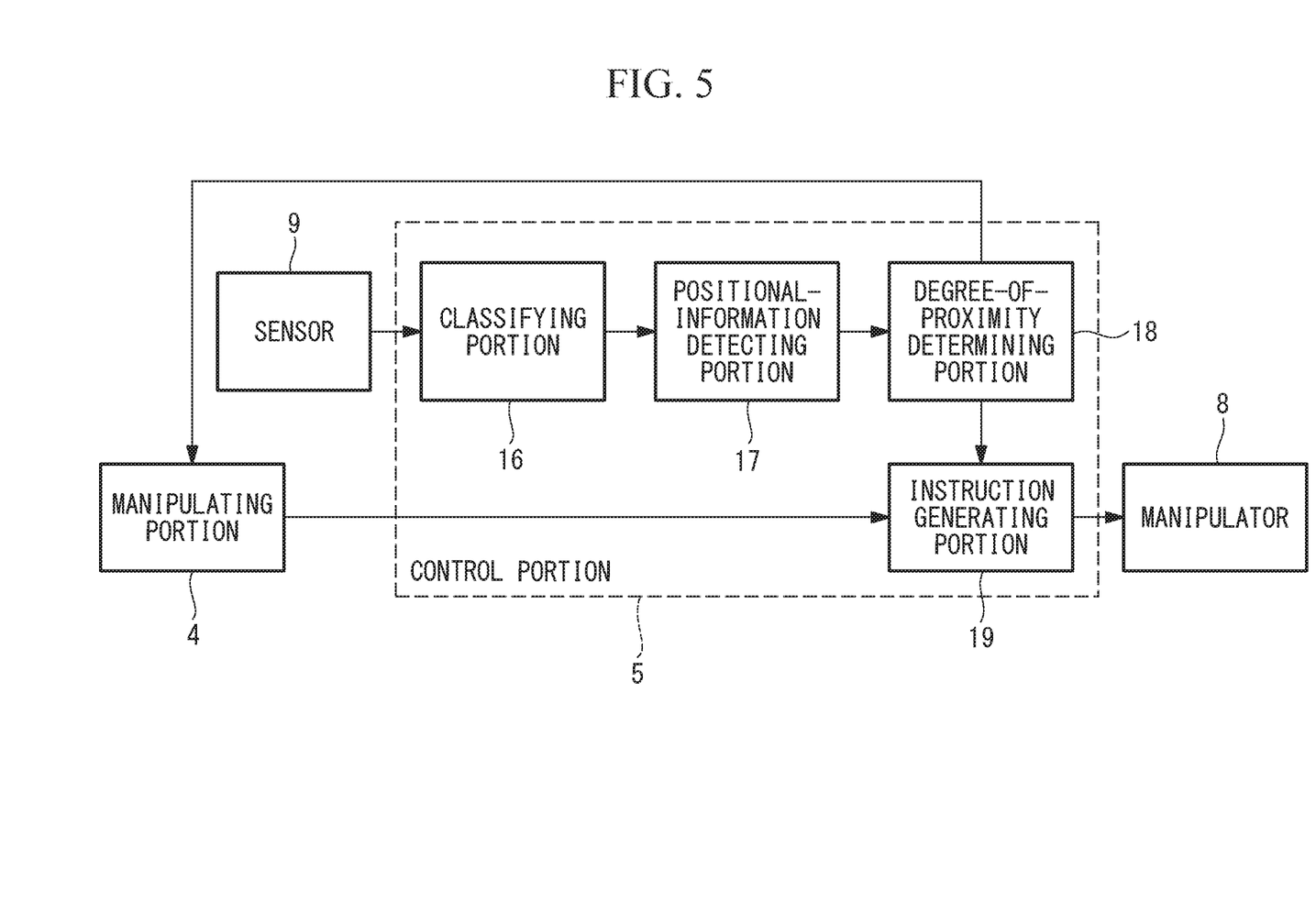
FIG. 5 is a block diagram showing a modification of FIG. 3.

Note that, with the medical manipulator system 1 according to this embodiment and the operating method thereof, in the case in which the distances between the manipulators 8 being manipulated and other objects are getting too close, the control portion 5 issues a notification about this fact; however, alternatively, or, in addition thereto, the control portion 5 may control the manipulators 8 so as to avoid interference. In this case, as shown in FIG. 5, determination results of the degree-of-proximity determining portion 18 are also transmitted to the instruction generating portion 19.

Figure 6:
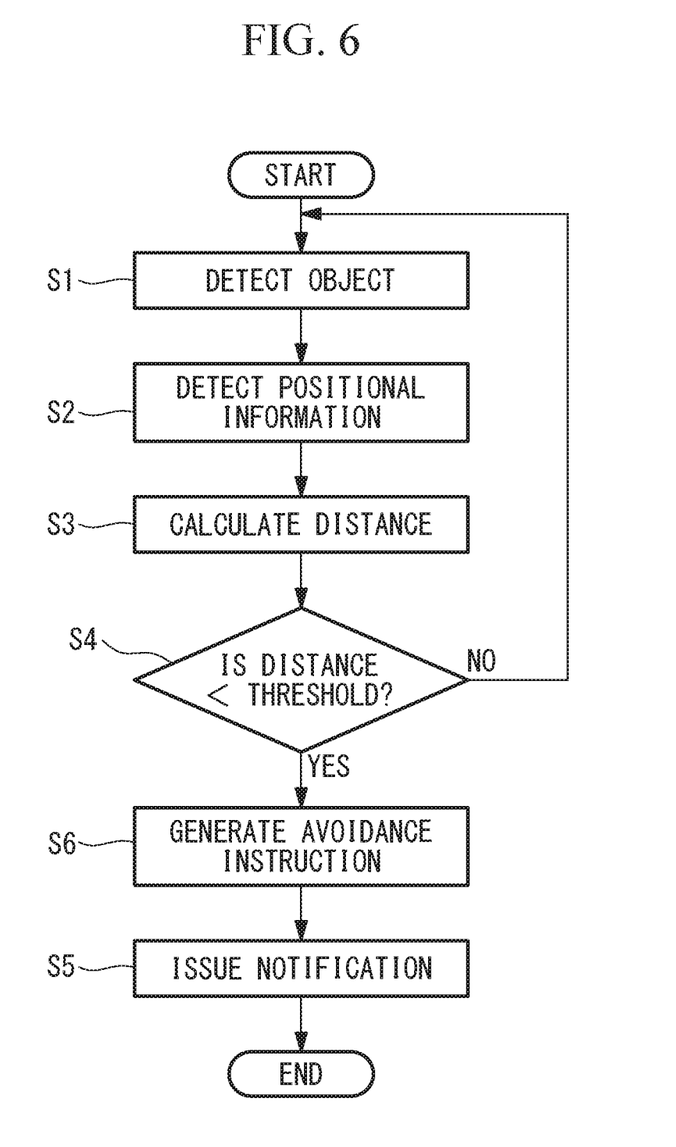
FIG. 6 is a flowchart showing a modification of FIG. 4.

Examples of the method of avoiding interference by means of the control portion 5 include, as shown in FIG. 6, first, generating, by means of the control portion 5, instruction signals for halting the motion of the manipulators 8 being manipulated (step S6). In this case, by issuing the notification on the monitor 14 in combination therewith, it is possible to notify the operator, who is performing the operation by viewing only the monitor 14, the reason why the treatment tool 11 is not moved in accordance with the manipulation inputs.

A second example is to generate, by means of the control portion 5, instruction signals for moving the manipulators 8 being manipulated away from other objects to which the manipulators 8 were getting close (FIG. 6, step S6). In this case, it is preferable that the manipulators 8 have one or more redundant degrees of freedom. In other words, the manipulators 8 each include an arm portion 8a at the proximal end and a wrist portion 8b at the distal end. By providing three joints in the arm portion 8a, it is possible to determine the position of the wrist portion 8b in the three-dimensional space. On the other hand, by providing three joints in the wrist portion 8b, it is possible to determine the position and orientation of the distal end of the treatment tool 11.

Also, by additionally providing the arm portion 8a with one or more joints (degrees of freedom), it is possible to move the individual linkages forming the arm portion 8a without moving the position and the orientation of the wrist portion 8b. In other words, in the case in which the manipulators 8 being manipulated are too close to other objects, the control portion 5 can cause only the arm portions 8a to be moved in directions away from other objects.

By doing so, it is possible for the operator who is viewing only the monitor 14 to continue manipulation without noticing the proximities between the manipulators 8 and the objects. Also, in the case in which it is not possible to avoid interference by moving the manipulators 8, the manipulators 8 may be halted, and a notification regarding this fact may be issued via the monitor 14.

After the manipulators 8 are halted and the notification indicating that the manipulators 8 and the objects are too close to each other is issued via the monitor 14, the halted state of the manipulators 8 may be canceled if the close-proximity state is eliminated by moving other objects or the like. In this case, it is preferable that the operator perform manipulation for canceling the halted state of the manipulators 8. By doing so, it is possible to avoid the problem in which the temporarily halted manipulators 8 suddenly start to move.

In addition, in this embodiment, although the control portion 5 determines the degrees of proximity for all objects detected by the sensor 9, alternatively, the objects to serve as targets for determining the degrees of proximity may be made selectable.

In other words, although, by connecting the treatment tool 11 and trocars 12 to the manipulators 8, the control portion 5 can determine the positions and the degrees of proximity thereof, since the treatment tool 11 and the trocars 12 are assumed to come into contact with the patient P, if the degrees of proximity to the patient P are determined every time, the notifications regarding the degrees of freedom would be constantly issued.

Therefore, so as not have to perform determination regarding the degrees of proximity between the patient P and the treatment tool 11 as well as the trocars 12, it is necessary to exclude said determination by means of the methods indicated below.

A first example is a method in which, in a stage before surgery, in which the patient P has been laid down on the bed 2 and the trocars 12 and the treatment tool 11 have been installed, the control portion 5 recognizes the treatment tool 11, the trocars 12, and the patient P on the basis of the image acquired by the sensor 9, stores this information in a storing portion (not shown), and, during treatment, excludes the stored patient P from the targets for determining the degrees of proximity with respect to the trocars 12 and the treatment tool 11.

A second example is a method in which, in a stage before surgery, in which the patient P has been laid down on the bed 2 and the trocars 12 and the treatment tool 11 have been installed, the control portion 5 recognizes the patient P and treatment tool 11 as well as the patient P and the trocars 12 on the basis of the image acquired by the sensor 9, stores this information in a storing portion (not shown), and, during treatment, excludes the stored patient P from the targets for determining the degrees of proximity with respect to the trocars 12 and the treatment tool 11.

A third example is a method in which, when the manipulating portion 4 and the manipulators 8 are operated in an interlinked manner, the control portion 5 determines that the patient P and the treatment tool 11 and the trocars 12 secured to the manipulators 8, which are objects detected by the sensor 9, are too close to each other, thus causing a notification to be issued. In that stage, by the operator giving instructions to allow interference, thereafter, it is possible to exclude the patient P from the targets for determining the degrees of proximity with respect to the manipulators 8.

In addition, in this embodiment, although the operator is notified via the monitor 14 of the manipulating portion 4 when the degrees of proximity exceed the predetermined threshold, alternatively, other notifying portions, such as a lamp, a speaker, etc. may be employed. In addition, by providing notifying portions, such as a lamp, a speaker, etc., in the manipulators 8, the assistant A other than the operator may be notified.

The above-described embodiment also leads to the following aspects.

An aspect of the present invention is a medical manipulator system including: a placement table on which a patient is placed; at least one manipulator that supports a treatment tool with which the patient placed on the placement table is treated, and that adjusts a position and an orientation of the treatment tool; a sensor that is disposed above the manipulator and the placement table, and that detects objects that are present in a predetermined area including the manipulator and the placement table; a degree-of-proximity determining portion that determines degrees of proximity between the objects detected by the sensor and the manipulator; and a notifying portion that, in a case in which the degrees of proximity determined by the degree-of-proximity determining portion exceed a predetermined threshold, issues a notification about this fact.

With this aspect, when the patient is placed on the placement table and the objects that are present in the predetermined area including the manipulator and the placement table are detected by the sensor disposed above the placement table, the degrees of proximity between the detected objects and the manipulator are determined by the degree-of-proximity determining portion. In the case in which the determined degrees of proximity exceed the predetermined threshold, a notification indicating this fact is issued by the notifying portion. By doing so, the operator manipulating the manipulator can recognize the fact that the manipulator and the objects in the periphery thereof are close to each other, and thus, it is possible to avoid interference between the objects and the manipulator by halting further manipulation of the manipulator.

In the above-described aspect, the medical manipulator system may include a storing portion that stores a specific area in the predetermined area, wherein the notifying portion may exclude the specific area from targets about which notifications are issued in a case in which degrees of proximity in the specific area exceed the threshold.

By doing so, even if the degrees of proximity between the objects and the manipulator exceed the threshold in the specific area stored in the storing portion, the notifying portion does not issue a notification. In other words, because, when treating the patient, the patient, which is one of the objects detected by the sensor, and the treatment tool at the distal end of the manipulator need to come into contact with each other, and thus, it would be bothersome and manipulation would be hindered if a notification is also issued about this contact; and therefore, it is possible to enhance the operability by storing the patient as the specific area.

Another aspect of the present invention is a medical manipulator system including: a placement table on which a patient is placed; at least one manipulator that supports a treatment tool with which the patient placed on the placement table is treated, and that adjusts a position and an orientation of the treatment tool; a sensor that is disposed above the manipulator and the placement table, and that detects objects that are present in a predetermined area including the manipulator and the placement table; a degree-of-proximity determining portion that determines degrees of proximity between the objects detected by the sensor and the manipulator; and a controller that, in a case in which the degrees of proximity determined by the degree-of-proximity determining portion exceed a predetermined threshold, controls the manipulator so as to avoid interference with the objects With this aspect, when the patient is placed on the placement table and the objects that are present in the predetermined area including the manipulator and the placement table are detected by the sensor disposed above the placement table, the degrees of proximity between the detected objects and the manipulator are determined by the degree-of-proximity determining portion. In the case in which the determined degrees of proximity exceed the predetermined threshold, the controller controls the manipulator so as to avoid interference with the objects, and thus, it is possible to avoid interference between the objects and the manipulator.

In the above-described aspect, the medical manipulator system may include the storing portion that stores the specific area in the predetermined area, wherein the control portion may control the manipulator so as to allow interference with the objects in a case in which the degrees of proximity in the specific area exceed the threshold.

By doing so, even if the degrees of proximity between the objects and the manipulator exceed the threshold in the specific area stored in the storing portion, the controller does not cause the manipulator to be moved so as to avoid interference. In other words, because, when treating the patient, the patient, which is one of the objects detected by the sensor, and the treatment tool at the distal end of the manipulator need to come into contact with each other, and thus, it is not possible to perform treatment in which this contact is avoided; and therefore, it is possible to reliably perform treatment by storing the patient as the specific area.

In the above-described aspect, the manipulator may have one or more redundant degrees of freedom.

By doing so, in the case in which the degrees of proximity between the objects and manipulator determined by the degree-of-proximity determining portion exceed the predetermined threshold, when the controller causes the manipulator to be moved, it is possible to move the manipulator while maintaining the position and the orientation of the treatment tool by utilizing the redundant degree of freedom. By doing so, it is possible to avoid interference while continuing treatment by using the treatment tool even if the manipulator is about to interfere with other objects during when performing treatment by using the treatment tool.

In the above-described aspect, the medical manipulator system may include a base portion that is disposed above the placement table, wherein the manipulator may be attached in the vicinity of an outer periphery of the base portion, and the sensor may be secured in the vicinity of a center of a bottom surface of the base portion.

By doing so, the manipulator is attached to the vicinity of the outer periphery of the base portion, which is disposed above the placement table, so as to be suspended therefrom, and thus, it is possible to access the patient placed on the placement table from above the patient. Thus, by using the sensor secured to the vicinity of the center of the bottom surface of the base portion, it is possible to detect the objects in the predetermined area including the manipulator and the patient on the placement table without being hindered by the manipulator itself.

In the above-described aspect, the medical manipulator system may include a base driving portion that moves the base portion in at least one of a horizontal direction and a vertical direction.

By doing so, by moving the base portion in at least one of the horizontal direction and the vertical direction by operating the base driving portion, it is possible to adjust the position of the manipulator with respect to the patient while maintaining the detection area of the sensor with respect to the manipulator.

Another aspect of the present invention is an operating method of a medical manipulator system with which a patient placed on a placement table is treated by using a treatment tool attached to at least one manipulator, the medical-manipulator-system operating method including: detecting, from above the manipulator and the placement table, objects that are present in a predetermined area including the manipulator and the placement table; determining degrees of proximity between the detected objects and the manipulator; and, in a case in which the determined degrees of proximity exceed a predetermined threshold, issuing a notification indicating this fact.

Another aspect of the present invention is an operating method of a medical manipulator system with which a patient placed on a placement table is treated by using a treatment tool attached to at least one manipulator, the medical-manipulator-system operating method including: detecting, from above the manipulator and the placement table, objects that are present in a predetermined area including the manipulator and the placement table; determining degrees of proximity between the detected objects and the manipulator; and, in a case in which the determined degrees of proximity exceed a predetermined threshold, controlling the manipulator so as to avoid interference with the objects.

The present invention affords an advantage in that it is possible not only to avoid interference between manipulators in the system, but also to avoid interference with objects outside the system.

REFERENCE SIGNS LIST 1 medical manipulator system
2 bed (placement table)
5 control portion
6 base portion
8 manipulator
9 sensor
10 base driving portion
11 treatment tool
14 monitor (notifying portion)
18 degree-of-proximity determining portion
P patient

The invention claimed is:

1. A medical manipulator system comprising:
a placement table on which a patient is placed;
at least one manipulator configured to support a treatment tool configured to treat the patient, the manipulator being configured to adjust a position and an orientation of the treatment tool;
a base portion configured to support the manipulator;
a sensor configured to detect objects which are present in a predetermined area including the manipulator and the placement table, the sensor being arranged at a bottom surface of the base portion separate from the at least one manipulator; and
a controller comprising at least one processor, wherein the at least one processor is configured to:
calculate degrees of proximity between the objects detected by the sensor and the manipulator, and
generate, in case that the calculated degrees of proximity exceed a predetermined threshold, a control signal for preventing interference between the objects and the manipulator.

2. The medical manipulator system according to claim 1, wherein the at least one processor is configured to:
receive data from the sensor,
recognize the objects in the predetermined area based on the data,
classify the recognized objects in accordance with predetermined attributes,
calculate positional information of the objects based on the data of the recognized objects and the classified attributes, and
calculate degrees of proximity with respect to the manipulator based on the positional information of the objects.

3. The medical manipulator system according to claim 1, wherein the control signal notifies the operator that the manipulator and the objects are close to each other.

4. The medical manipulator system according to claim 1, wherein the control signal causes the manipulator to be moved so as to prevent interference of the manipulator with the objects.

5. The medical manipulator system according to claim 4, wherein the manipulator has one or more redundant degrees of freedom.

6. The medical manipulator system according to claim 5, wherein the control signal moves the manipulator by prioritizing the one or more redundant degrees of freedom.

7. The medical manipulator system according to claim 1,
wherein the manipulator is located adjacent to an outer periphery of the base portion, and
the sensor is located adjacent to a center of the bottom surface of the base portion.

8. The medical manipulator system according to claim 1, wherein the base portion is configured to support the manipulator at a position higher than the placement table.

9. The medical manipulator system according to claim 1, wherein the sensor is provided at a position in the base portion at which the manipulator and the placement table can be looked upon from thereabove.

10. A controller for a medical manipulator system, the medical manipulator system comprising a placement table, at least one manipulator configured to support a treatment tool, and a sensor configured to detect objects which are present in a predetermined area including the manipulator and the placement table, the controller comprising:
at least one processor, wherein the at least one processor is configured to:
calculate degrees of proximity between the objects detected by the sensor, arranged at a bottom surface of the base portion separate from the at least one manipulator, and the manipulator, and
generate, in case that the calculated degrees of proximity exceed a predetermined threshold, a control signal for preventing interference between the objects and the manipulator.

11. The controller according to claim 10, wherein the processor is configured to:
receive data from the sensor,
recognize the objects in the predetermined area based on the data,
classify the recognized objects in accordance with predetermined attributes,
calculate positional information of the objects based on the classified attributes and the recognized objects, and
calculate degrees of proximity with respect to the manipulator based on the calculated positional information.

12. The controller according to claim 10, wherein the control signal causes the manipulator to be moved so as to prevent interference of the manipulator with the objects.

13. A method of controlling a medical manipulator system, the medical manipulator system comprising a placement table, at least one manipulator configured to support a treatment tool, and a sensor configured to detect objects which are present in a predetermined area including the manipulator and the placement table, the method comprising:
calculating degrees of proximity between the objects detected by the sensor, arranged at a bottom surface of the base portion separate from the at least one manipulator, and the manipulator, and
generating, in case that the calculated degrees of proximity exceed a predetermined threshold, a control signal for preventing interference between the objects and the manipulator.

14. The method of controlling the medical manipulator system according to claim 13, wherein the control signal causes the manipulator to be moved so as to prevent interference of the manipulator with the objects.

15. The method of controlling the medical manipulator system according to claim 13, further comprising:
   receiving data from the sensor;
   recognizing the objects in the predetermined area based on the data;
   classifying the recognized objects in accordance with predetermined attributes;
   calculating positional information of the objects based on the classified attributes and the recognized objects; and
   calculating degrees of proximity with respect to the manipulator based on the calculated positional information.

16. The medical manipulator system according to claim 1, wherein the sensor is a 3D camera.

* * * * *